United States Patent [19]

Piez et al.

[11] Patent Number: 4,774,227
[45] Date of Patent: Sep. 27, 1988

[54] COLLAGEN COMPOSITIONS FOR BONE REPAIR CONTAINING AUTOGENEIC MARROW

[75] Inventors: Karl A. Piez, Menlo Park, Calif.; Shlomo Weintraub, Tel-Aviv, Israel

[73] Assignees: Collagen Corporation, Palo Alto, Calif.; Ramot Ltd., Tel-Aviv, Israel

[21] Appl. No.: 829,809

[22] Filed: Feb. 14, 1986

[51] Int. Cl.[4] ............... A61K 37/02; A61K 35/28; A61F 2/28
[52] U.S. Cl. ............... 514/21; 424/95; 514/801; 128/92 YG; 128/92 YR; 128/DIG. 8
[58] Field of Search ............... 424/95; 514/801, 21; 128/92 YG, 92 YR, DIG. 8

[56] References Cited

U.S. PATENT DOCUMENTS 4,347,234 8/1982 Wahlig et al. ............... 514/801
4,394,370 10/1984 Jeffries ............... 424/95

OTHER PUBLICATIONS

Salama et al., J. Bone Joint Surg., 55, pp. 402–417, 1973.

*Primary Examiner*—J. R. Brown
*Assistant Examiner*—Jacqueline M. Stone
*Attorney, Agent, or Firm*—Ciotti & Murashige, Irell & Manella

[57] ABSTRACT

A composition which combines autogenic bone marrow with a suspension of purified atelopeptide reconstituted collagen is used to repair bone defects in mammals.

8 Claims, No Drawings

COLLAGEN COMPOSITIONS FOR BONE REPAIR CONTAINING AUTOGENEIC MARROW

TECHNICAL FIELD

The invention relates to the repair of defects in human bone. More particularly, it relates to the use of especially efficacious compositions for filling these defects. The compositions comprises purified fibrillar reconstituted collagen with a preparation of autogeneic bone marrow.

BACKGROUND ART

The use of autogeneic bone particles and/or bone marrow is widespread and well known in the art. See, for example, Salama, R., et al, *J Bone Joint Surg* (Br) (1973) 55: 402–417. Bone marrow has also been combined with biodegradable ceramic for periodontal defect repair (Levin, M.P., et al, *J Biomed Mater Res* (1975) 9: 183–195). The marrow or cancellous bone appears quite effective in mediating repair.

The use of collagen preparations for the repair of bone defects has also been extensively reported. The use of Collagenfleece ®, in particular, which is a freeze-dried, pepsin-treated preparation from pig skin, sterilized by gamma irradiation (as described in U.S. Pat. No. 4,066,083) has been reported by Krekeler, B. G., et al, *J Oral Surg* (1981) 10:suppl. 1: 151;; Joos, U., et al, *Biomaterials* (1980) 1: 23–26; Zetzmann, D., et al, *Schweiz Mschr Sabnhelik* (1982) 92: 119; and Springorum, H. W., et al, *Z Orthorp* (1977) 115: 686. Other collagen preparations were used by Jaffee, A., et al, *Arch Oral Biol* (1978) 23: 415; ibid (1982) 27: 999, and by Cucin, R. L., et al, *NY State J Med* (1979) 1856. The use of atelopeptide fibrillar bovine collagen as a composition for conductive bone repair was disclosed in U.S. Ser. No. 752,447, filed 5 July 1985, assigned to the same assignee, and incorporated herein by reference. In addition, collagen has been used in conjunction with a factor extractable from bone which mediates inductive bone repair as disclosed by Jeffries in U.S. Pat. No. 4,394,370 and in U.S. Ser. No. 664,158, filed Oct. 24, 1984, assigned to the same assignee and incorporated herein by reference.

While it seems clear that bone marrow derived from the same individual, or, at worst, from an individual closely related, is helpful in repairing bone injuries or defects, it is a problem to keep the bone marrow in any but very small defects. Thus, bone marrow is not widely used as such. The material of choice is cancellous bone, which consists of a porous bone containing bone marrow. The problems with cancellous bone are that a second operation may be required to obtain it and it may be in short supply.

DISCLOSURE OF THE INVENTION

The invention provides a composition for repair of bone defects that permits the advantages inherent in a natural tissue such as bone marrow to be utilized while overcoming the problems of handling. It has been found that suitable collagen preparations are capable of adding sufficient body to keep the mixture in a defect and provide a biocompatible environment to induce bone repair by the cells in bone marrow.

Accordingly, in one aspect, the invention is directed to a method to mediate the repair of bone defects which utilizes a composition containing, in addition to autogeneic bone marrow, an extender which comprises reconstituted fibrillar atelopeptide collagen. Additional materials such as binders may optionally be added. In another aspect, the invention relates to compositions which are useful in this method, and to processes for preparing these compositions.

MODES OF CARRYING OUT THE INVENTION

A. The Autogeneic Marrow Component

The compositions for use in the method of the invention are comprised of an autogeneic tissue-derived component and a collagen component. The autogenic component is derived from either the same individual who bears the defect to be repaired or from an individual sufficiently closely related genetically that the materials derived from this individual are not immunogenic in the recipient. It is recognized that, except for the same individual or an identical twin, the degree of genetic relatedness represents a continuum, and that methods for predicting in advance whether or not sufficient close relationship is present to prevent immunogenicity are not entirely precise. However, current practice does operate within these parameters and attempts to evaluate genetic matching for surgical transplantation procedures, with varying degrees of success. In general, as used herein, "autogeneic" refers to material either derived from the same person (or his twin) or from an individual judged by standard and commonly practiced techniques and criteria to be sufficiently closely related to provide a workable source of such material.

The methods of obtaining this evaluation of "autogeneic" character and/or excising bone marrow from such individuals are standard in the art and do not form part of the invention. The bone marrow would generally be used directly in the form obtained.

B. The Collagen

The collagen portion of the preparation is a nonimmunogenic form of a reconstituted fibrillar preparation, such as, for example, commercially available preparations used for soft tissue repair. These preparations include Zyderm ® collagen implant (ZCI), which is available from Collagen Corporation, Palo Alto, CA, in concentrations of 35 mg/ml and 65 mg/ml. In general, these suitable collagen preparations are prepared from animal skins, although any source of predominantly type I collagen can be used. The preparation will include treatment with a suitable proteolytic enzyme to remove the telopeptide portions extending beyond the triple helical segments, which telopeptide portions are responsible for the native cross-linking between helices and for at least a portion of the immunogenicity of the preparation.

In a suitable procedure, a mammalian skin preparation, preferably bovine skin, is depilated and ground or minced to form a finely divided preparation which is solubilized under nondenaturing conditions by dispersing it in an aqueous medium and digesting with a proteolytic enzyme other than a collagenase, preferably an enzyme that is active at low pH. Dilute acid solutions of, for example, HCl or of carboxylic acids, such as acetic, malonic, or lactic acids, are used at low temperature with a pH normally in the range of 1.5–5, depending on the enzyme used. A preferred procedure is to disperse the comminuted tissue in HCl to a concentration of 1–5 g/l at a pH of about 2 at 20° C. After the tissue is dispersed, the enzyme is added and the mixture is incubated to permit the enzyme to digest the telopeptide and other solubilizable components of the tissue.

Suitable enzymes for the digestion of the telopeptides which do not attack the triple helical portion of the collagen include pepsin, papain and trypsin, preferably pepsin, with an enzyme concentration in the range of 0.1%-10% by weight based on the collagen content of the tissue. The incubation period can last from about 1 day to 2 weeks and the process of solubilization may be monitored by determining the viscosity of the solution. Once the viscosity reaches a substantially constant level, the solubilization is complete, and the enzyme is deactivated and removed.

After denaturation of the enzyme, the solution is treatedto remove the denatured enzyme and the digested portions of the tissue by various techniques, and combinations thereof including, for example, dialysis, precipitation, and filtration. The soluble components including the collagen are segregated from sedimented or filtered solids and concentrated, optionally fractionated on ion exchange chromatography, and further concentrated to produce a substantially pure atelopeptide collagen solution. Typical concentration levels of the collagen in the solution are 1-10 mg/ml.

The collagen in solution is reconstituted to a fibrillar form by neutralizing the solution at reduced temperatures, preferably about 10°-25° C., preferably under hypotonic conditions relative to physiological ionic strength. The neutralizing solution may be added directly or, preferably, by dialysis of the solubilized collagen against it. Ionic strengths of about 0.03-0.1, preferably 0.06, are used, and the pH is raised by adding an appropriate base or buffer such as disodium phosphate or sodium hydroxide to a level at which the collagen in solution reaggregates into fibrils. Fibril formation occurs under these conditions at a pH in the range of about 5-10, and the final pH is preferably in the range of of 7-8. The duration of the fibril formation step is normally in the range ½-18 hours.

Optionally, the reconstituted atelopeptide collagen gel suspension may be cross-linked with a cross-linking agent such as, for example, various aldehydes such as formaldehyde, acetaldehyde, glyoxalpyruvic aldehyde, and dialdehyde starch, preferably glutaraldehyde. During the cross-linking reaction, the collagen concentration is kept at about 0.1-10 mg/ml, preferably 1-5 mg/ml. Following cross-linking, the reaction may be quenched with compounds which have functional groups that react with the functional groups of the cross-linking agent to form water soluble adducts. In particular, compounds containing free amino groups, such as, for example, glycine, are usable in this respect. Optionally, the excess crosslinking agent may be removed by washing.

The foregoing general preparation procedures are typical of those used to prepare suitable collagen for the composition of the invention. However, the specific procedure used is not significant so long as the resulting preparation is substantially free of the telopeptide portions, has been reconstituted, is fibrillar, and is basically pure collagen uncontaminated with materials coexisting with the collagen in its native environment. These characteristics are required for biocompatibility.

The collagen suspension that results is typically a suspension in aqueous solution at a concentration of 10-100 mg/ml, preferably about 35 or 65 mg/ml. A favorable suspension medium is isotonic saline, but other buffer solutions or aqueous solutions which permit the collagen suspension to be stabilized are also acceptable.

C. The Mixture

The compositions of the invention are formed by simple mixing of the suspensions of the bone marrow with the suspension of the fibrillar collagen. The suspensions are mixed in a volume ratio of 5-50% a marrow in admixture with the collagen suspension.

The preferred ratios depend on a number of factors, including the nature of the defect, the size of the defect, the metabolism of the subject, and judgment of the practitioner repairing the defect. In general, the compositions of the invention comprise a wide range of ratios of bone marrow to the collagen carrier.

The compositions of the invention are implanted into a bone defect using standard surgical procedures for cancellous bone preparations. Such procedures are well known to orthopedic, reconstructive and dental surgery practitioners and are applied using the generally understood practices of the these professions. In addition, if the collagen used is injectable, as is ZCI, the mixture will also be injectable. Therefore, in the case of bone defects which are not surgically opened, the mixture may be transcutaneously injected.

Defects which are suitable subjects for implantation by the compositions of the invention include bone fractures, bone structures requiring supplementation, such as alveolar ridge augmentation, periodontal defects, congenital bone defects and surgical bone loss. Any defect which is a suitable substrate for filling with an autogeneic cancellous bone is a suitable substrate for the composition of the invention, except that the increased availability of materials in the composition of the invention may make possible the treatment of defects which were too large and require too much material to permit filling with autogeneic cancellous bone.

In summary, the compositions contain a suspension of bone marrow in admixture with a suspension of an atelopeptide pure reconstituted fibrillar collagen. The bone marrow must be autogeneic as defined above; that is, it must be derived from the same individual or from an individual sufficiently closely related that the marrow is nonimmunogenic in the recipient. The collagen portion, on the other hand, may be derived from any source. The removal of the telopeptides diminishes the immunogenicity sufficiently that even xenogeneic sources may be used. The reconstituted fibrillar nature of the collagen preparation permits conduction of the bone growth which is induced by the bone marrow in the composition.

EXAMPLES

The following example is intended to illustrate but not to limit the invention. In this illustration, various compositions falling within the description of the invention are used to repair an artificial bone defect in rats, and compared with the results of corresponding implants using either collagen or bone marrow alone.

Rats were provided with bone defects by removal of a 6 mm segment of the femur. The bone was fixed with a plate and pins in a standard manner. Defects were filled with either bone marrow alone, or bone marrow in combination with collagen. The results were compared for either no treatment or for treatment with collagen alone. The implants were examined by radiology, giving the results after various intervals up to 12 weeks in Table 1.

The observations were graded on a scale of 0 to 4, where 0 represented no change and 4 represented complete filling of the defect with a medullary canal. As seen in Table 1, the combination of bone marrow prepared from the individual subject rats with ZCI (a 35 mg/ml suspension of atelopeptide fibrillar reconstituted collagen) was compared with the effect of this collagen alone, of marrow alone and of cancellous bone.

As shown in Table 1, ZCI alone was relatively ineffective in repair of the defect. Over a long time period (12 weeks), the combinations of bone marrow with collagen were superior to marrow alone, although marrow alone was reasonably effective.

It can be imagined that in larger defects, marrow alone would be less effective. Cancellous bone, the standard material now used, was somewhat less effective than ZCI plus marrow.

TABLE 1

|  | 3 Week | Union*  6 Week | 9 Week | 12 Week |
|---|---|---|---|---|
| ZCI | 0 (14) | 0.21 ± 0.80 (14) | 0.54 ± 1.33 (13) | 0.83 ± 1.59 (12) |
| Control | 0 (18) | 0 | 0.21 ± 0.80 (14) | 0.21 ± 0.81 (14) |
| ZCI + marrow | 0 (14) | 2.07 ± 1.26 (13) | 3.00 ± 0.58 (13) | 3.83 ± 0.39 (12) |
| Marrow alone | 0.86 ± 1.51 (14) | 1.43 ± 1.72 (14) | 1.38 ± 1.85 (13) | 2.27 ± 1.79 (11) |
| Cancellous Bone | 0.60 ± 1.06 (15) | 1.71 ± 1.64 (14) | 2.23 ± 1.59 (13) | 3.00 ± 1.54 (12) |

*Scale 0–4, ±S.D., estimated from x-rays
Number of rats is shown in parentheses

We claim:

1. A method to mediate the repair of bone defects which comprises placing into said defect a composition containing reconstituted fibrillar atelopeptide collagen and autogeneic bone marrow.

2. The method of claim 1 wherein the collagen is supplied as an aqueous suspension containing 10–100 mg/ml and is 50%–95% of said composition by volume.

3. The method of claim 1 wherein the collagen is of xenogeneic origin.

4. The method of claim 3 wherein the collagen is of bovine origin.

5. The method of claim 1 wherein the composition is injected into the defect.

6. A composition for the repair of bone defects which comprises
    (a) an aqueous suspensions containing 10–100 mg/ml of reconstituted fibrillar atelopeptide purified collagen, and
    (b) autogeneic bone marrow.

7. The composition of claim 6 wherein the collagen suspension comprises 50%–95% by volume of the composition.

8. The composition of claim 6 which is an injectable suspension.

* * * * *